United States Patent
Zhang et al.

(10) Patent No.: US 12,195,522 B2
(45) Date of Patent: Jan. 14, 2025

(54) RABIES VIRUS MONOCLONAL ANTIBODY 2F2 AND UNIVERSAL RABIES VIRUS ANTIBODY RAPID DETECTION TEST PAPER

(71) Applicants: Longhu Laboratory, Zhengzhou (CN); Zhengzhou University, Zhengzhou (CN)

(72) Inventors: Gaiping Zhang, Zhengzhou (CN); Aiping Wang, Zhengzhou (CN); Peiyang Ding, Zhengzhou (CN); Yaning Sun, Zhengzhou (CN); Yumei Chen, Zhengzhou (CN); Jianguo Zhao, Zhengzhou (CN); Hongliang Liu, Zhengzhou (CN); Haili Wang, Zhengzhou (CN)

(73) Assignees: LONGHU LABORATORY, Zhengzhou (CN); ZHENGZHOU UNIVERSITY, Zhengzhou (CN)

( * ) Notice: Subject to any disclaimer, the term of this patent is extended or adjusted under 35 U.S.C. 154(b) by 21 days.

(21) Appl. No.: 18/069,456

(22) Filed: Dec. 21, 2022

(65) Prior Publication Data

US 2024/0092874 A1    Mar. 21, 2024

Related U.S. Application Data

(63) Continuation of application No. PCT/CN2022/118626, filed on Sep. 14, 2022.

(30) Foreign Application Priority Data

Sep. 8, 2022    (CN) .......................... 2022107045258

(51) Int. Cl.
*C07K 16/10*    (2006.01)
*G01N 33/543*    (2006.01)
*G01N 33/569*    (2006.01)

(52) U.S. Cl.
CPC ........ *C07K 16/10* (2013.01); *G01N 33/54388* (2021.08); *G01N 33/56983* (2013.01); *G01N 2469/20* (2013.01)

(58) Field of Classification Search
CPC .................................................... C07K 16/10
See application file for complete search history.

(56) References Cited

FOREIGN PATENT DOCUMENTS

| CN | 107860920 A | * | 3/2018 | ....... G01N 33/56983 |
|---|---|---|---|---|
| CN | 109959789 A | | 7/2019 | |
| CN | 113252893 A | | 8/2021 | |
| CN | 114989296 A | | 9/2022 | |
| SG | 127494 A1 | | 12/2006 | |

* cited by examiner

*Primary Examiner* — Elizabeth C. Kemmerer
*Assistant Examiner* — Ashley H. Gao
(74) *Attorney, Agent, or Firm* — Muncy, Geissler, Olds & Lowe, P.C.

(57) ABSTRACT

The present invention provides a rabies virus monoclonal antibody 2F2 and universal rabies virus antibody rapid detection test paper and belongs to the technical field of biological detection. An amino acid sequence of the monoclonal antibody 2F2 is shown as SEQ ID No. 1. The monoclonal antibody 2F2 provided by the present invention specifically binds to rabies virus G proteins, and preparation of the monoclonal antibody 2F2 into test paper has the advantages of rapidity, accuracy, sensitivity, specificity and low cost.

8 Claims, 3 Drawing Sheets

Specification includes a Sequence Listing.

RABIES VIRUS MONOCLONAL ANTIBODY 2F2 AND UNIVERSAL RABIES VIRUS ANTIBODY RAPID DETECTION TEST PAPER

TECHNICAL FIELD

The present invention belongs to the technical field of biological detection, in particular to a rabies virus monoclonal antibody 2F2 and universal rabies virus antibody rapid detection test paper.

STATEMENT REGARDING SEQUENCE LISTING

The sequence listing associated with this application is provided in text format in lieu of a paper copy and is hereby incorporated by reference into the specification. The name of the XML file containing the sequence listing is sl.xml. The XML file is 5,626 bytes; was created on Dec. 21, 2022; and is being submitted electronically via EFS-Web.

BACKGROUND

Rabies is a kind of anthropozoonosis with a case fatality rate close to 100%. Rabies virus (RV) belongs to the Rhabdoviridae family and belongs to the same genus of rabies as Lagos bat virus, Mokola virus, Duvenhage virus, European bat rabies virus type 1, European bat rabies virus type 2 and Australian bat rabies virus. The RV is a single minus-strand RNA virus, of which one end is round and convex and the other end is flat and concave, and is shaped like a bullet with a diameter of 65-80 nm and a length of about 130-240 nm. The RV is easily inactivated by sunlight, ultraviolet rays, formaldehyde, mercuric quaternary amine compounds (such as bromogeramine), lipid solvents, 75% alcohol and on the like, and the virus can be inactivated by inactivating a RV suspension for 30-60 min at 56° C. or for 2 min 100° C. The virus may remain active for several years at −70° C. or after being lyophilized and placed at 0-4° C. Infected tissues may be stored in 50% glycerol for testing. The RV mainly contains five proteins, namely glycoprotein (G), nucleoprotein (N), dimerase (L), phosphoprotein (NS) and matrix (M). The glycoprotein G is a main protective antigen, which may induce a body to produce a neutralizing antibody against virus attacks.

The rabies may be prevented by standardized pre-exposure and post-exposure treatment. Rabies vaccination is an important treatment means. After vaccine immunization, a titer level of the rabies virus neutralizing antibody in serum may be determined to evaluate whether vaccination has reached a protective level or not. The standard methods recommended by the World Health Organization for detection of the rabies virus neutralizing antibody (RVNA) include a rapid fluorescent focus inhibition test (RFFIT) and a mouse neutralization test (MNT). Since the MNT requires to use animals is cumbersome in operation and is time-consuming, while the RFFIT requires the use of a fixed rabies strain CVS-11 and involves live virus operation and the like, popularization of these two methods is limited.

SUMMARY

In view of this, the purpose of the present invention is to provide a rabies virus monoclonal antibody 2F2 and universal rabies virus antibody rapid detection test paper. The monoclonal antibody 2F2 provided by the present invention specifically binds to rabies virus G proteins, and preparation of the monoclonal antibody 2F2 into the test paper has the advantages of rapidity, accuracy, sensitivity, specificity and low cost.

In order to achieve the above-mentioned purpose of the present invention, the present invention provides the following technical solutions:

the present invention provides a monoclonal antibody 2F2 recognizing the rabies virus G proteins, and an amino acid sequence of the monoclonal antibody 2F2 is shown as SEQ ID No.1.

The present invention further provides application of the monoclonal antibody 2F2 described in the above technical solution in preparing a reagent for detecting rabies virus.

The present invention further provides universal rabies virus antibody rapid detection test paper which includes: a sample pad, a binding pad, a detection membrane and a water absorption pad sequentially overlapped on a support plate, wherein a test line and a quality control line are sprayed on the detection membrane; and the monoclonal antibody 2F2 according to claim 1 is sprayed on the quality control line.

Preferably, the monoclonal antibody 2F2 is sprayed in a form of a monoclonal antibody 2F2 solution, and a concentration of the monoclonal antibody 2F2 solution is 0.5 mg/mL.

Preferably, the monoclonal antibody 2F2 solution is sprayed by 1 μL/cm.

Preferably, the test line is sprayed with SPA, the SPA is sprayed in a form of a SPA solution, and a concentration of the SPA solution is 0.5 mg/mL; and the SPA solution is sprayed by 1 μL/cm.

Preferably, the binding pad is sprayed with colloidal gold-labeled rabies virus G proteins.

Preferably, the rabies virus G proteins are sprayed in a form of a rabies virus G protein solution, and a concentration of the rabies virus G protein solution is 1 mg/ml; and the rabies virus G protein solution is sprayed by 15 μL/cm.

Preferably, a distance between the quality control line and the test line is 0.5 cm.

Preferably, an overlapping distance of an overlap joint is 1-2 mm.

The present invention prepares the monoclonal antibody 2F2 into test paper, and the detection principle of the test paper is that:

immunochromatographic detection test paper for the rabies virus antibody uses a RV G recombinant protein and a monoclonal antibody thereof, and is designed and assembled according to a modern immunological technology and a chromatography technology; during chromatography of a serum sample to be tested, an antibody to be tested in the sample and the gold-labeled G recombinant proteins on the binding pad bind and are then captured by the SPA on the test line (T line); excess gold-labeled G recombinant proteins are captured by the 2F2 monoclonal antibody on the quality control line (C line); and thus two lines appear.

A detection limit of the test paper provided by the present invention for detecting rabies virus positive serum may reach 1:12800; and a specific detection result shows that the test paper does not cross-react with positive serum of other viruses of the same genus.

DESCRIPTION OF THE EMBODIMENTS

Figure 1:
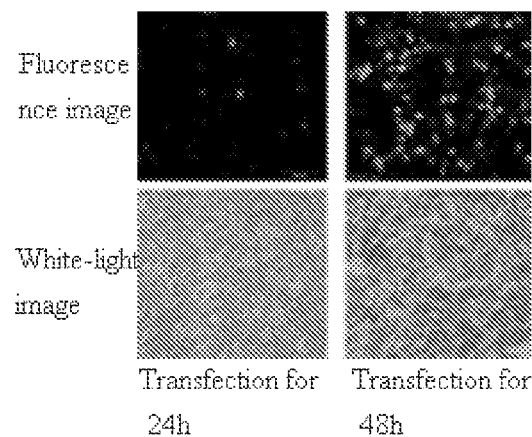
FIG. 1 is a diagram showing lentivirus packaging.

The present invention provides a monoclonal antibody 2F2 recognizing rabies virus G proteins. An amino acid sequence of the monoclonal antibody 2F2 is shown as SEQ ID No. 1, specifically as follows:

EAQSGAGLVASPQSVKLTCTATGFNITKDYHWVWIRQFPGEQLEWMGWID

SESGDISYNPSLKFQISITADTSWNTAFLDLNSVTSEDTAVYYCNAVSLG

DQASISCRSSQSLLHSDGNTYLDWYLQKPGQSPKLLIYTSSFHRFSGVPD

RFSGSGSGTDFTLKISRVEAEDLGIYFCSQSTLLPPTFGGGTKLEIKRI.

The bold part represents a heavy chain variable region, and the underlined part represents a light chain variable region.

The present invention further provides application of the monoclonal antibody 2F2 described in the above technical solution in preparing a reagent for detecting a rabies virus. The present invention does not specifically limit the type of the reagent prepared by the monoclonal antibody 2F2, and those skilled in the art can routinely prepare the monoclonal antibody 2F2.

The present invention further provides universal rabies virus antibody rapid detection test paper which includes: a sample pad, a binding pad, a detection membrane and a water absorption pad sequentially overlapped on a support plate, wherein a test line and a quality control line are sprayed on the detection membrane; and the monoclonal antibody 2F2 described in the above technical solution is sprayed on the quality control line.

In the present invention, the monoclonal antibody 2F2 is preferably sprayed in a form of a monoclonal antibody 2F2 solution, and a concentration of the monoclonal antibody 2F2 solution is preferably 0.5 mg/mL. In the present invention, the monoclonal antibody 2F2 solution is preferably sprayed by 1 μL/cm. In the present invention, a PBS buffer is preferably adopted to prepare the monoclonal antibody 2F2 solution.

In the present invention, the test line is preferably sprayed with SPA, the SPA is preferably sprayed in a form of a SPA solution, and a concentration of the SPA solution is preferably 0.5 mg/mL. In the present invention, the SPA solution is preferably sprayed by 1 μL/cm. In the present invention, the PBS buffer is preferably adopted to prepare the SPA solution.

In the present invention, the binding pad is preferably sprayed with colloidal gold-labeled rabies virus G proteins. The present invention does not specifically limit a method for labeling the rabies virus G proteins with colloidal gold, and those skilled in the art can only require make operation according to conventional techniques. In the present invention, the rabies virus G proteins are preferably sprayed in a form of a rabies virus G protein solution, and a concentration of the rabies virus G protein solution is preferably 1 mg/ml; and the rabies virus G protein solution is preferably sprayed by 15 μL/cm. In the present invention, a distance between the quality control line and the test line is preferably 0.5 cm. In the present invention, an overlapping distance of an overlap joint is preferably 1-2 mm.

The technical solutions provided by the present invention will be described in detail below with reference to the embodiments, but should not be construed as limiting the protection scope of the present invention.

Embodiment 1

Expression and Purification of RV G Recombinant Proteins

1. Synthesis of Target Gene

Figure 2:
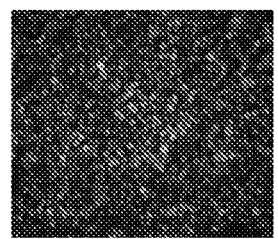
FIG. 2 is a diagram showing a CHO cell line stably expressing rabies virus G proteins.

Referring to sequence information of a rabies virus strain G-protein published in GenBank (GenBank: E02022.1), after a sequence was optimized into codons preferred by CHO, a gene sequence of the RV G proteins were synthesized by Shanghai Bioengineering Co., Ltd., a 6×His tag gene sequence was added, and the sequence was cloned into a pLVX-IRES-ZsGreen1 lentiviral vector to construct eukaryotic recombinant expression pLVX-G-IRES-Zs-Green1, referred to as pLVX-G. Lentiviruses were packaged (as shown in FIG. 1), CHO cells were transduced, and CHO/G positive cells were screened (as shown in FIG. 2).

2. Expression and Identification of G Proteins (1) Mass culture of cells: CHO/G cells were inoculated to a 50 mL shake flask for culture the at 120 rpm, and a growth density of the cells was detected by cell counting. When the cell culture density remained the same, the cells in the 50 mL shake flask were transferred into a 500 mL shake flask for high-density culture and were counted every day; when the cell density is greater than 1.5 times the initial density, an additive solution of a SMS CHO—SUFI medium was started to be added at a rate of 1.5% and was added every day; and when the cell density remained unchanged, or the cell death rate began to increase, the additive solution of the SMS CHO—SUPI medium was stopped from adding, a cell suspension was collected, and a supernatant was collected by centrifugation;

(2) 100 μL of the above cell supernatant was taken, 25 μL of 5× Loading buffer was added to prepare protein electrophoresis samples, SDS-PAGE analysis was conducted, and expression of RV G recombinant proteins were detected. A result of SDS-PAGE shows that the RV G recombinant proteins have a target band at 65 KD, indicating that the RV G recombinant proteins are solubly expressed.

(3) The collected cell supernatant was identified by Western blot. The specific steps are as follows: gel after SDS- PAGE was electrotransferred to a nitrocellulose membrane (NC membrane) at 15 V in a membrane transfer machine; the NC membrane was blocked with PB ST containing 5% nonfat dry milk overnight at 4° C.; His monoclonal antibody as a primary antibody was adopted, diluted at 1:5000 and incubated for 1 h at the room temperature; HRP-labeled goat anti-mouse IgG as a secondary antibody was adopted, diluted at 1:5000 and incubated for 1 h at the room temperature; and an AEC color developing solution was added under a dark condition, and a color developing result was observed. A Western blot result shows that the RV G recombinant proteins have a band at 65 KD, which is consistent with the expected result.

3. Purification of RV G Recombinant Proteins

Since having a 6×His tag, the RV G recombinant proteins are purified through a nickel column. After the culture supernatant is filtered with a 0.45 μm filter, the proteins are purified by nickel column affinity chromatography. The specific purification steps are as follows:

(1) 2 mL of nickel column filler was pipetted and added to an installed protein purification column, and after the filler settled, an upper spacer was carefully added; and a control valve was opened, 20% ethanol flowed out, and the column was continuously washed with 10 mL of deionized water.

(2) A control valve of a protein purification device was adjusted to make the flow rate stable; and after the flow rate was adjusted, the column was flushed with 10 mL or more of equilibration buffer (20 mM phosphate buffer, pH 7.4, 0.5 M NaCl) containing 20 mM imidazole at 1 mL/min.

(3) A sonicated supernatant filtered by a membrane filter was added to the above equilibrated column in batches with 5 mL each time, the control valve was adjusted to make the flow rate not exceed 1 mL/min, percolate was quickly collected, sample loading was repeated for 2-3 times, and the last percolate was collected and stored at −20° C. for later use.

(4) The RV G recombinant protein was purified by washing the column with a washing buffer containing 200 mM imidazole (20 mM phosphate buffer, pH 7.4, 0.5 M NaCl) to remove impure proteins.

(5) Finally, 10 mL of elution buffer containing 500 mM imidazole was added to the column to elute a target protein; the control valve was adjusted to decrease the flow rate of the liquid as much as possible; and the eluted liquid was collected into 1.5 mL EP tubes with 1 mL per tube, a protein concentration of each tube was measured with a microplate reader and marked, and the tubes were placed at −20° C. for later use.

(6) After purification, the nickel column was washed with 20 mL of ddw, then washed with a NaOH solution (1 mol/L) washed with ddw again and finally stored in 20% ethanol in a refrigerator at 4° C.

(7) 5× Loading Buffer was added to the eluate collected after purification and boiled for 10 min, and a purification result was analyzed by 12% SDS-PAGE.

Figure 3:
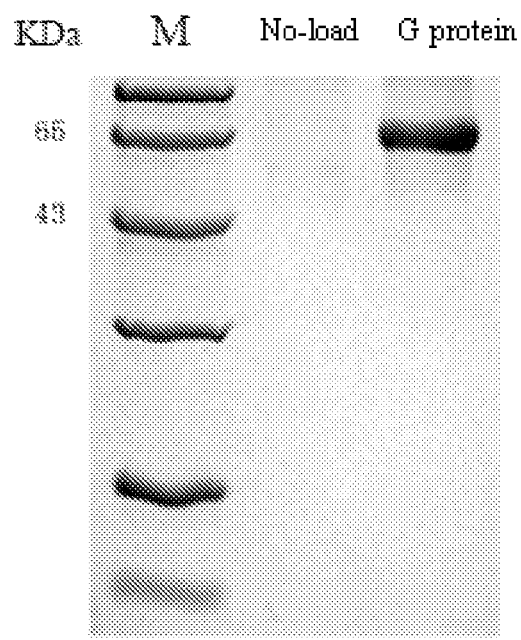
FIG. 3 is a diagram showing purified RV G recombinant proteins.

(8) An SDS-PAGE result shows that the target band of the purified RV G recombinant proteins is at 65 KD, which is consistent with the expected result, and a purity of the RV G recombinant proteins can reach 90% or above (as shown in FIG. 3).

(9) A concentration of the RV G recombinant proteins was determined as 1.3 mg/mL by a BCA method; and the purified proteins were subpackaged and stored in the refrigerator at −80° C. for later use.

An nucleotide sequence of a protein G (SEQ ID No.2) is as follows:

ATGATCCCTCAGGTGCTGCTGTTTGTGCCTCTGCTGGTGTTCTCTTCTTG
TTTTGGAAAGTTTCCTATCTACACCATCCCTGATAAGCTGGGCCCTTGGT
CTCCTATCGATATCCACCACCTGAGCTGTCCTAACAACCTGGTGGTGGAG
GATGAGGGCTGTACCAACCTGTCTGGCTTTTCTTACATGGAGCTGAAGGT
GGGCTACATCTCCGCCATCAAGGTGAATGGCTTCACATGCACCGGCGTGG
TGACAGAGGCCGAGACATACACCAACTTTGTGGGATACGTGACCACAACC
TTCAAGAGGAAGCACTTTAGACCTATGCCTGATGCCTGTAGAGCCGCTTA
CAACTGGAAGATGGCCGGCGACCCAAGATACGAGGAGTCCCTGCACAACC
CTTACCCTGATTACCACTGGCTGAGAACAGTGAAAACAACCAAGGAGTCT
CTGGTCATCATCAGCCCTTCTGTGGCCGATCTGGACCCTTACGATAAGAG
CCTGCACTCTAGAGTGTTTCCCGGCGGCAAGTGCTCTGGCATCACAGTGA
GTTCTACCTGTTGTAGCACCAACCACGATTACACAATCTGGATGCCTGAG
AACCCTAGACTGGGCACCAGCTGTGACATCTTCACAAACTCTAGGGGCAA
GAGAGCTTCTAAGGGAGGAAAGACATGTGGCTTTGTGGATGAGAGGGGCC
TGTATAAGTCTCTGAAGGGAGCTTGTAAGATGAAGCTGTGTGGAGTGCTG
GGACTGAGACTGATGGATGGCACCTGGGTGGCTATCCAGACCTCTGATGA
GATTAAGTGGTGTAGCCCTGACCAGCTGGTGAACCTGCACGACTTTCACA
GCGATGAGATCGAGCACCTGGTGGTGGAGGAGCTGGTGAAGAAGAGAGAG
GAGTGTCTGGATGCCCTGGAGACAATCATGACCACAAAGAGCGTGTCTTT
TAGAAGATTGAGCCATCTGAGAAAGCTGGTGCCTGGATTTGGAAAGGCCT
ACACAATCTTCAACAAGACACTGATGGAGGCTGATGCCCACTACAAGAGC
ATCAGGACATGGAACGAGATCATTCCTTCTAAGGGCTGTCTGAGAGTGGG
CGGCAGATGTCACCCTCACGTGAACGGCGTGTTCTTCAACGGCATCATCC
TGGGACCTGATGGCCACGTGCTGATCCCTGAAATGCAGAGCTCTCTGCTG
CACCAGCACATGGAGCTGCTGGAGTCCTCTGTGATCCCTCTGATGCATCC
TCTGGCCGATCCTTCTACCGTGTTTAAGGATGGCGATGAGGCCGAGGATT
TTGTGGAGGTGCACCTGCCTGATGTGCATAAGCAGATCTCTGGCGTGGAT
CTGGGCCTGCCTAACTGGGAAAGTACCATCACCACCACCACCACTAA.

An amino acid sequence of a protein G (SEQ ID No.3) is as follows:

MIPQVLLFVPLLVFSSCFGKFPIYTIPDKLGPWSPIDIHHLSCPNNLVVE
DEGCTNLSGFSYMELKVGYISAIKVNGFTCTGVVTEAETYTNFVGYVTTT
FKRKHFRPMPDACRAAYNWKMAGDPRYEESLHNPYPDYHWLRTVKTTKES
LVIISPSVADLDPYDKSLHSRVFPGGKCSGITVSSTCCSTNHDYTIWMPE
NPRLGTSCDIFTNSRGKRASKGGKTCGFVDERGLYKSLKGACKMKLCGVL
GLRLMDGTWVAIQTSDEIKWCSPDQLVNLHDFHSDEIEHLVVEELVKKRE
ECLDALETIMTTKSVSFRRLSHLRKLVPGFGKAYTIFNKTLMEADAHYKS
IRTWNEIIPSKGCLRVGGRCHPHVNGVFFNGIILGPDGHVLIPEMQSSLL

-continued

HQHMELLESSVIPLMHPLADPSTVFKDGDEAEDFVEVHLPDVHKQISGVD

LGLPNWGKYHHHHHH.

Embodiment 2

Preparation of Monoclonal Antibody

1. Animal Immunization (1) The purified RV G recombinant proteins as an immunogen were mixed with a Freund's complete adjuvant in a ratio of 1:1, and then a mixture was emulsified for first immunization.

(2) Three female BALB/c mice aged 4 to 8 weeks were immunized with two immunogens by subcutaneous injection at multiple points on the back with an immunization dose of 50 μg/mouse.

(3) The BALB/c mice were boosted with the same method and dose after emulsification of the Freund's incomplete adjuvant and immunizing antigen every two weeks for a total of 4 times of immunization.

(4) After 4 times of immunization, tail vein blood was collected to measure a specific antibody titer against RV G recombinant proteins, the mice with higher titer were selected, and BALB/c mice were hyperimmunized with the RV G recombinant proteins without an adjuvant by intraperitoneal injection 3-4 days before cell fusion with the dose of 100 μg/mouse.

2. Cell Fusion and Screening of Positive Clones

Spleen cells of the immunized mice were fused with mouse myeloma cells SP2/0 in a ratio of 8:1 by cell amount by a method of polyethylene glycol, and the fused cells were screened with an HAT selection medium; and after 12 days of fusion, positive hybridoma cells were initially screened by an indirect ELISA method with the RV G recombinant proteins as a coating antigen.

The steps of the indirect ELISA method are as follows:

(1) The RV G recombinant proteins were diluted into a coating solution with a concentration of 2 μg/mL with a CBS buffer, and an ELISA plate was coated with 100 μl/well and incubated for 2 h at 37° C.

(2) The coating solution was discarded, the plate was washed with PBST and pat-dried, and the ELISA plate with 200 μl/well was blocked with 5% nonfat milk and incubated for 2 h at 37° C.

(3) The blocking solution was discarded, the plate was washed with the PB ST and pat a hybridoma supernatant (primary antibody) was added to the ELISA plate with 100 μl/well for incubation for 30 min at 37° C.

(4) The primary antibody was discarded, and the plate was washed for 7 times with the PB ST and pat-dried.

(5) Diluted HRP-labeled goat anti-mouse IgG (secondary antibody) was added to reaction wells with 100 μl/well for incubation for 30 min at 37° C.

(6) The secondary antibody was discarded, and the plate was rinsed for 7 times with the PBST and pat-died.

(7) 100 μl of real-time prepared TMB color developing solution was added to each well for reaction in a dark room for 5 min.

(8) 100 μl of $H_2SO_4$ (2 M) was added to each well to stop the reaction.

(9) The $OD_{450}$ value of each well was read by a microplate reader.

3. Subcloning of Hybridoma Cells by Limiting Dilution Method

Positive wells with an $OD_{450}$ value above 1.0 were selected, the above-mentioned positive hybridoma cells were diluted to about 10 cells/ml with a 1640 medium containing 10% fetal bovine serum and added to a 96-well plate pre-laid with 100 μl feeder cells with 100 μl per well, and the 96-well plate was placed in a 5% $CO_2$ incubator for one week at 37° C.; further, the positive hybridoma cells were screened by the indirect ELISA method; and subcloning was conducted for a total of 2-3 times until a hybridoma cell strain 2F2 that stably secretes an anti-RV G recombinant protein monoclonal antibody was obtained, and positive monoclonal cell strains obtained by screening were subjected to expanded culture and were cryopreserved with $1-2\times10^6$/tube.

4. Identification of Monoclonal Hybridoma Cell Strains

The established monoclonal hybridoma cell strains were continuously cultured for 3 months and recovered from liquid nitrogen cryopreservation repeatedly to identify the stability of the hybridoma cells. A result shows that the obtained four monoclonal hybridoma cell strains are good in stability.

Figure 4:
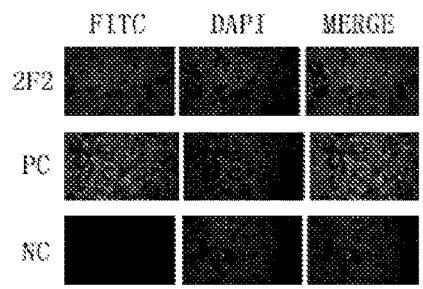
FIG. 4 is a diagram showing IFA results.
Figure 5:
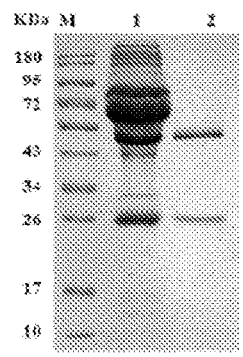
FIG. 5 is a diagram showing results of purifying a monoclonal antibody.

The reactivity of a 2F2 monoclonal antibody supernatant is identified with RV G protein by IFA method. A pcDNA3.1-RV G recombinant plasmid was transfected into 293T cells to transiently express the RV G proteins; after fixation with methanol, the 2F2 monoclonal antibody supernatant was incubated with the primary antibody for 1 h at 37° C., and a plate was washed with PBST for 7 times and pat-dried; an FITC-labeled goat anti-mouse antibody was incubated with the secondary antibody for 1 h at 37° C., and a plate was washed with the PBST for 7 times and pat-dried; and fluorescence was observed under an inverted microscope. A result shows that the 2F2 monoclonal antibody (SEQ ID No. 1) has good reactivity with the RV G proteins (FIG. 4).

5. Preparation of Monoclonal Antibody by In Vivo Induced Ascites

Multiparous female BALB/c mice were selected, injected with 500 μl of sterile Freund's incomplete adjuvant intraperitoneally and injected with the obtained monoclonal hybridoma cells 2F2 with an injection volume of 1×10 6 cells intraperitoneally one week later; and after another week, ascites was extracted after abdomens of the mice were enlarged, a supernatant was collected after centrifugation for 10 min at 6000 rpm, and the ascites was purified by an ammonium caprylic sulfate method. The specific steps are as follows:

(1) Intermediate layer liquid of the above-mentioned ascites was taken after centrifugation for 20 min at 6000 rpm and 4° C. and diluted by 5 times with acetate-sodium acetate (6 mmol/L).

(2) a pH value of the solution in the step (1) was adjusted to about 4.5 with 5 mol/L NaOH, a volume of the added NaOH solution was recorded, and stirring was conducted gently for 30 min at a room temperature.

(3) N-caprylic acid was added dropwise at the room temperature, and stirring was conducted while dropping to make a final concentration be 25 µL/mL; and at this time, the liquid became turbid, stirring was continued for 30 min at the room temperature, centrifugation was conducted for 30 min at 4° C. and 6000 rpm, and the intermediate layer liquid was taken.

(4) A medium-speed filter paper was wetted in a funnel with a PBS solution, the supernatant collected in the previous step was slowly filtered in the filter paper, and a filtrate was collected.

(5) The collected filtrate was mixed with 10×PBS solution at a ratio of 9:1, and a pH value was adjusted to 7.4.

(6) The obtained liquid was transferred to a refrigerator at 4° C. for cooling, 0.2778 g/mL of solid ammonium sulfate was added, stirring was conducted while adding, and addition was completed by 3 times within 30 min.

(7) The solution obtained in the previous step was centrifuged for 20 min at 4° C. and 6000 rpm, a supernatant was poured off, 600 µL of 1×PBS solution was added, and a product was put into a dialysis bag after precipitates were completely dissolved for dialysis for 1-2 days at 4° C.

(8) After dialysis, the purified ascites was centrifuged for 10 min at 6000 rpm and 4° C., and a supernatant was collected, subpackaged into small tubes and placed at −80° C. for later use.

Embodiment 3

Preparation and application of immunochromatographic detection test paper for rabies virus antibody This embodiment provides immunochromatographic test paper for detecting a rabies virus antibody, and the detection test paper includes RV G recombinant proteins and a 2F2 monoclonal antibody provided by the present invention.

1. Preparation of Gold-Labeled Antigen (1) Preparation of Colloidal Gold 100 mL of ultrapure water was taken and put in a 500 mL clean conical flask, and 1 mL of 1% (w/v) chloroauric acid solution was added for boiling; 1 mL of 1% (w/v) sodium citrate solution freshly prepared was quickly added under stirring, and a mixture was boiled for about 3 min until a color of the solution changed from yellow to amaranth and continued to be boiled for 2 min; and after the solution was cooled to a room temperature, the ultrapure water was supplemented to 100 mL, and a pH value was adjusted to 9.0 with 0.2 mol/L $K_2CO_3$, and the solution was stored in the dark at 4° C. for later use.

(2) Determination of Optimal Labeled Protein Concentration

G proteins to be labeled were taken and diluted in a microplate with 30 µL of ultrapure water at ratios of 1:2, 1:4, 1:8 . . . respectively; 125 µL of colloidal gold solution was added to each well and left for still standing for 5 min at the room temperature; 125 µL of 1 mol/L NaCl solution was added; and a color of each well changes from red to blue as a protein concentration decreases.

The highest dilution of the protein that does not turn blue serves as the optimal labeling concentration of colloidal gold.

(3) Colloidal Gold Labeling of Proteins 2 mL of proteins G to be labeled with the optimal protein concentration (12 µg/ml) were taken, 10 mL of colloidal gold solution (pH 9.0) was added for quick mixing, and action was conducted for 10-15 min at the room temperature; 20 mmol/L sodium borate solution containing 10% (w/v) bovine serum albumin (BSA), with a volume of 10% of that of a mixture, was added for quick mixing, and action was conducted for 10-15 min at the room temperature; centrifugation was conducted at 15000 g for 30 min at 4° C., abd a supernatant was carefully removed; resuspension and precipitation were conducted with 20 mmol/L sodium borate solution containing 1% (w/v) BSA, centrifugation was conducted as above, and a supernatant was discarded; and washing was repeated once, resuspension and precipitation were conducted in 1 mL of 20 mmol/L sodium borate solution containing 1% (w/v) BSA, and a product was stored at 4° C. for later use.

2. Development of Test Paper (1) Preparation of Detection Membrane

A nitrocellulose detection membrane (NC membrane) was placed on a platform of an XYZ 3000 spot spray instrument and fixed with a strip; each of the 2F2 monoclonal antibody and a SPA solution were diluted to 0.5 mg/mL with the PBS buffer, filtered through a 0.22 µm filter and then spot-sprayed to the center of the nitrocellulose detection membrane at 1 µL/cm to form blots of a quality control line (C line) and test lines (T lines); a distance between the test line and the test line and a distance between the test line and the quality control line are 0.5 cm; and the detection membrane was placed in a drying box for 30 min at 42° C. or after being naturally dried at the room temperature, the detection membrane was stored in a dry and sealed mode.

(2) Preparation of Binding Pad

Glass wool was put on the platform of the XYZ 3000 spot spray instrument and fixed with a strip; 1 mL of gold-labeled proteins was taken, and 2 mL of 20 mmol/L sodium borate solution (pH 8.0) containing 2% (w/v) BSA, 3% (w/v) sucrose, 0.6 mol/L NaCl, 0.2% Tween 20 (v/v) and 0.1% (w/v) sodium azide were added; the gold-labeled G protein solution (1 mg/ml) was spot-sprayed to the glass wool by 15 µL/cm; the glass wool was placed in a drying oven at 50° C. for 30 min for drying; and the binding pad was placed in a plastic bag, a desiccant was added, and the plastic bag was stored at 4° C. in an airtight state for later use.

(3) Preparation of Sample Pad

Glass wool strips was soaked into the PBS (pH 7.2) solution containing 0.1 mol/LNaCl, 0.2% Tween 20 (v/v) and 0.1% (w/v) sodium azide and dried in a drying oven for 30 min at 50° C.; and the sample pad was placed in a plastic bag, the desiccant was added, and the plastic bag was stored at the room temperature in an airtight state for later use.

(4) Preparation of Water Absorption Pad

A water absorption pad was put in a plastic bag, the desiccant was added, and the plastic bag was stored at the room temperature in the airtight state for later use.

(5) Preparation of Support Plate

A double-sided tape was attached to a PVC support plate to prepare the support plate.

(6) Assembly of Test Paper

Figure 6:
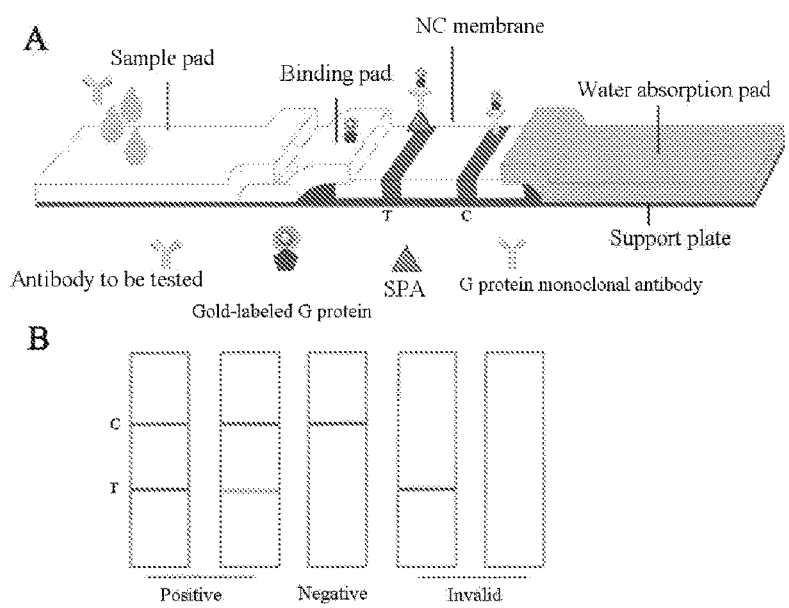
FIG. 6 is a schematic diagram of immunochromatographic rapid detection test paper for a rabies virus antibody.

The above materials were assembled into a test paper plate through a LM5000 test paper assembler or manually. Firstly, the detection membrane was pasted in the center of the support plate, then the binding pad containing gold-labeled G proteins and the sample pad were pasted on the sample end of the detection membrane in turn with every two layers overlapping by 1-2 mm, and then the water absorption pad was pasted to the other end of the detection membrane and overlapped the detection membrane by 1-2 mm (as shown in FIG. 6).

(7) Detection Principle

The immunochromatographic detection test paper for the rabies virus antibody used the RV G recombinant proteins and the monoclonal antibody thereof and was designed and assembled according to a modern immunological technology and a chromatography technology; and during chromatography of a serum sample to be tested, an antibody to be tested in the sample and the gold-labeled G recombinant protein on the binding pad bound and were then captured by SPA on the test line (T line), excess gold-labeled G recombinant proteins were captured by the 2F2 monoclonal antibody on the quality control line (C line), and thus two lines appeared.

3. Detection of Clinical Samples

Figure 7:
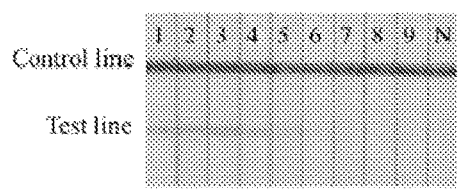
FIG. 7 is a diagram showing detection limits of immunochromatographic rapid detection test paper for a rabies virus antibody: 1. 1:400; 2. 1:800; 3. 1:1600; 4. 1:3200; 5. 1:6400; 6. 1:12800; 7. 1:25600; 8. 1:51200; 9. 1:102400; N:PBS.
Figure 8:
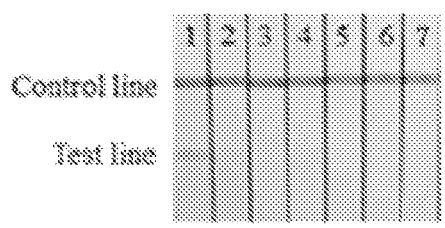
FIG. 8 is a diagram showing the specificity of immunochromatographic rapid detection test paper for a rabies virus antibody: 1: rabies virus; 2: Lagos bat virus; 3: Mokola virus; 4: Duvenhage virus; 5: European bat rabies virus type 1; 6: European bat rabies virus type 2; and 7: Australian bat rabies virus.

The rabies virus antibody detection immunochromatographic test paper prepared by the present invention is used to simultaneously detect standard positive serum of rabies virus, Lagos bat virus, Mokola virus, Duvenhage virus, European bat rabies virus type 1, European bat rabies virus type 2 and Australian bat rabies virus respectively. A detection result shows that a detection limit of the rabies virus antibody detection immunochromatographic test paper of the present invention for detecting rabies virus positive serum may reach 1:12800 (FIG. 7); and a specific detection result shows that the test paper does not cross-react with other virus-positive serum of the same genus. The above results show that the rabies virus antibody detection immunochromatographic test paper prepared by the present invention has high sensitivity and specificity (FIG. 8).

The above embodiments are only the preferred embodiments of the present invention. It should be pointed out that those skilled in the art can also make several improvements and modifications without departing from the principles of the present invention, and these improvements and modifications should also be regarded as falling within the protection scope of the present invention.

```
                            Sequence Table
<110> Longhu Modern Immunology Laboratory
Zhengzhou University
<120> Rabies virus monoclonal antibody 2F2 and
universal rabies virus antibody rapid
detection test paper.
<141> 2022-06-13
<160> 3
<170> SIPO Sequence Listing 1.0
<210> 1
<211> 199
<212> PRT
<213> Artificial Sequence
<400> 1
Glu Ala Gln Ser Gly Ala Gly Leu Val Ala Ser Pro Gln Ser Val Lys
1               5                   10                  15

Leu Thr Cys Thr Ala Thr Gly Phe Asn Ile Thr Lys Asp Tyr His Trp
            20                  25                  30

Val Trp Ile Arg Gln Phe Pro Gly Glu Gln Leu Glu Trp Met Gly Trp
        35                  40                  45

Ile Asp Ser Glu Ser Gly Asp Ile Ser Tyr Asn Pro Ser Leu Lys Phe
    50                  55                  60

Gln Ile Ser Ile Thr Ala Asp Thr Ser Trp Asn Thr Ala Phe Leu Asp
65                  70                  75                  80

Leu Asn Ser Val Thr Ser Glu Asp Thr Ala Val Tyr Tyr Cys Asn Ala
                85                  90                  95

Val Ser Leu Gly Asp Gln Ala Ser Ile Ser Cys Arg Ser Ser Gln Ser
            100                 105                 110

Leu Leu His Ser Asp Gly Asn Thr Tyr Leu Asp Trp Tyr Leu Gln Lys
        115                 120                 125

Pro Gly Gln Ser Pro Lys Leu Leu Ile Tyr Thr Ser Ser Phe His Arg
    130                 135                 140

Phe Ser Gly Val Pro Asp Arg Phe Ser Gly Ser Gly Ser Gly Thr Asp
145                 150                 155                 160

Phe Thr Leu Lys Ile Ser Arg Val Glu Ala Glu Asp Leu Gly Ile Tyr
                165                 170                 175
```

Phe Cys Ser Gln Ser Thr Leu Leu Pro Pro Thr Phe Gly Gly Gly Thr
        180                 185                 190

Lys Leu Glu Ile Lys Arg Ile
    195

<210> 2
<211> 1398
<212> DNA
<213> Artificial Sequence
<400> 2
atgatccctc aggtgctgct gtttgtgcct ctgctggtgt tctcttcttg ttttggaaag    60
tttcctatct acaccatccc tgataagctg ggcccttggt ctcctatcga tatccaccac   120
ctgagctgtc ctaacaacct ggtggtggag gatgagggct gtaccaacct gtctggcttt   180
tcttacatgg agctgaaggt gggctacatc tccgccatca aggtgaatgg cttcacatgc   240
accggcgtgg tgacagaggc cgagacatac accaactttg tgggatacgt gaccacaacc   300
ttcaagagga agcactttag acctatgcct gatgcctgta gagccgctta caactggaag   360
atggccggcg acccaagata cgaggagtcc ctgcacaacc cttaccctga ttaccactgg   420
ctgagaacag tgaaaacaac caaggagtct ctggtcatca tcagcccttc tgtggccgat   480
ctggaccctt acgataagag cctgcactct agagtgtttc cggcggcaa gtgctctggc   540 atcacagtga gttctacctg ttgtagcacc aaccacgatt acacaatctg gatgcctgag   600
aaccctagac tgggcaccag ctgtgacatc ttcacaaact ctaggggcaa gagagcttct   660
aagggaggaa agacatgtgg ctttgtggat gagaggggcc tgtataagtc tctgaaggga   720
gcttgtaaga tgaagctgtg tggagtgctg ggactgagac tgatggatgg cacctgggtg   780
gctatccaga cctctgatga gattaagtgg tgtagccctg accagctggt gaacctgcac   840
gactttcaca gcgatgagat cgagcacctg gtggtggagg agctggtgaa gagagagag    900 gagtgtctgg atgccctgga gacaatcatg accacaaaga gcgtgtcttt tagaagattg   960
agccatctga gaaagctggt gcctggattt ggaaaggcct acacaatctt caacaagaca  1020
ctgatggagg ctgatgccca ctacaagagc atcaggacat ggaacgagat cattccttct  1080
aagggctgtc tgagagtggg cggcagatgt caccctcacg tgaacggcgt gttcttcaac  1140
ggcatcatcc tggacctga tggccacgtg ctgatccctg aaatgcagag ctctctgctg  1200
caccagcaca tggagctgct ggagtcctct gtgatccctc tgatgcatcc tctggccgat  1260
ccttctaccg tgtttaagga tggcgatgag gccgaggatt ttgtggaggt gcacctgcct  1320
gatgtgcata gcagatctc tggcgtggat ctgggcctgc taactgggg aaagtaccat  1380 caccaccacc accactaa                                                 1398

<210> 3
<211> 465
<212> PRT
<213> Artificial Sequence
<400> 3
Met Ile Pro Gln Val Leu Leu Phe Val Pro Leu Leu Val Phe Ser Ser
1               5                   10                  15

Cys Phe Gly Lys Phe Pro Ile Tyr Thr Ile Pro Asp Lys Leu Gly Pro
            20                  25                  30

Trp Ser Pro Ile Asp Ile His His Leu Ser Cys Pro Asn Asn Leu Val
        35                  40                  45

Val Glu Asp Glu Gly Cys Thr Asn Leu Ser Gly Phe Ser Tyr Met Glu
    50                  55                  60

-continued

Sequence Table

Leu Lys Val Gly Tyr Ile Ser Ala Ile Lys Val Asn Gly Phe Thr Cys
65              70              75              80

Thr Gly Val Val Thr Glu Ala Glu Thr Tyr Thr Asn Phe Val Gly Tyr
            85              90              95

Val Thr Thr Thr Phe Lys Arg Lys His Phe Arg Pro Met Pro Asp Ala
            100             105             110

Cys Arg Ala Ala Tyr Asn Trp Lys Met Ala Gly Asp Pro Arg Tyr Glu
            115             120             125

Glu Ser Leu His Asn Pro Tyr Pro Asp Tyr His Trp Leu Arg Thr Val
            130             135             140

Lys Thr Thr Lys Glu Ser Leu Val Ile Ile Ser Pro Ser Val Ala Asp
145             150             155             160

Leu Asp Pro Tyr Asp Lys Ser Leu His Ser Arg Val Phe Pro Gly Gly
            165             170             175

Lys Cys Ser Gly Ile Thr Val Ser Ser Thr Cys Cys Ser Thr Asn His
            180             185             190

Asp Tyr Thr Ile Trp Met Pro Glu Asn Pro Arg Leu Gly Thr Ser Cys
            195             200             205

Asp Ile Phe Thr Asn Ser Arg Gly Lys Arg Ala Ser Lys Gly Gly Lys
            210             215             220

Thr Cys Gly Phe Val Asp Glu Arg Gly Leu Tyr Lys Ser Leu Lys Gly
225             230             235             240

Ala Cys Lys Met Lys Leu Cys Gly Val Leu Gly Leu Arg Leu Met Asp
            245             250             255

Gly Thr Trp Val Ala Ile Gln Thr Ser Asp Glu Ile Lys Trp Cys Ser
            260             265             270

Pro Asp Gln Leu Val Asn Leu His Asp Phe His Ser Asp Glu Ile Glu
            275             280             285

His Leu Val Val Glu Glu Leu Val Lys Lys Arg Glu Glu Cys Leu Asp
290             295             300

Ala Leu Glu Thr Ile Met Thr Thr Lys Ser Val Ser Phe Arg Arg Leu
305             310             315             320

Ser His Leu Arg Lys Leu Val Pro Gly Phe Gly Lys Ala Tyr Thr Ile
            325             330             335

Phe Asn Lys Thr Leu Met Glu Ala Asp Ala His Tyr Lys Ser Ile Arg
            340             345             350

Thr Trp Asn Glu Ile Ile Pro Ser Lys Gly Cys Leu Arg Val Gly Gly
            355             360             365

Arg Cys His Pro His Val Asn Gly Val Phe Phe Asn Gly Ile Ile Leu
            370             375             380

Gly Pro Asp Gly His Val Leu Ile Pro Glu Met Gln Ser Ser Leu Leu
385             390             395             400

His Gln His Met Glu Leu Leu Glu Ser Ser Val Ile Pro Leu Met His
            405             410             415

Pro Leu Ala Asp Pro Ser Thr Val Phe Lys Asp Gly Asp Glu Ala Glu
            420             425             430

Asp Phe Val Glu Val His Leu Pro Asp Val His Lys Gln Ile Ser Gly
            435             440             445

| Sequence Table |
|---|
| Val Asp Leu Gly Leu Pro Asn Trp Gly Lys Tyr His His His His His<br>  450             455           460<br><br>His<br> 465 |

SEQUENCE LISTING

```
Sequence total quantity: 3
SEQ ID NO: 1             moltype = AA   length = 199
FEATURE                  Location/Qualifiers
source                   1..199
                         mol_type = protein
                         organism = synthetic construct
SEQUENCE: 1
EAQSGAGLVA SPQSVKLTCT ATGFNITKDY HWVWIRQFPG EQLEWMGWID SESGDISYNP    60
SLKFQISITA DTSWNTAFLD LNSVTSEDTA VYYCNAVSLG DQASISCRSS QSLLHSDGNT   120
YLDWYLQKPG QSPKLLIYTS SFHRFSGVPD RFSGSGSGTD FTLKISRVEA EDLGIYFCSQ   180
STLLPPTFGG GTKLEIKRI                                                199

SEQ ID NO: 2             moltype = DNA   length = 1398
FEATURE                  Location/Qualifiers
source                   1..1398
                         mol_type = other DNA
                         organism = synthetic construct
SEQUENCE: 2
atgatccctc aggtgctgct gtttgtgcct ctgctggtgt tctcttcttg ttttggaaag    60
tttcctatct acaccatccc tgataagctg ggcccttggt ctcctatcga tatccaccac   120
ctgagctgtc ctaacaacct ggtggtggag gatgagggct gtaccaacct gtctggcttt   180
tcttacatgg agctgaaggt gggctacatc tccgccatca aggtgaatgg cttcacatgc   240
accggcgtgg tgacagaggc cgagacatac accaactttg tgggatacgt gaccacaacc   300
ttcaagagga agcactttag acctatgcct gatgcctgta gagccgctta caactggaag   360
atggccggcg acccaagata cgaggagtcc ctgcacaacc cttaccctga ttaccactgg   420
ctgagaacag tgaaaacaac caaggagtct ctggtcatca tcagcccttc tgtggccgat   480
ctggaccctt acgataagag cctgcactct agagtgtttc ccggcggcaa gtgctctggc   540
atcacagtga gttctacctg tttgtagcacc aaccacgatt acacaatctg gatgcctgag   600
aaccctagac tgggcaccag ctgtgacatc ttcacaaact ctaggggcaa gagagcttct   660
aagggaggaa agacatgtgg ctttgtggat gagaggggcc tgtataagtc tctgaaggga   720
gcttgtaaga tgaagctgtg tggagtgctg ggactgagac tgatggatgg cacctggtg    780
gctatccaga cctctgatga gattaagtgg tgtagccctg accagctggt gaacctgcac   840
gacttccaca gcgatgagat cgagcacctg gtggtggagg agctggtgaa gaagagagag   900
gagtgtctgg atgccctgga gacaatcatg accacaaaga gcgtgtcttt tagaagattg   960
agccatctga aaagctggt gcctggattt ggaaaggcct cacacaatct caacaagaca   1020
ctgatggagg ctgatgccca ctacaagagc atcaggacat ggaacgagat cattccttct   1080
aagggctgtc tgagagtggg cggcagatgt caccctcacg tgaacggcgt gttcttcaac   1140
ggcatcatcc tgggacctga tggccacgtg ctgatccctg aaatgcagag ctctctgctg   1200
caccagcaca tggagctgct ggagtcctct gtgatccctc tgatgcatcc tctggccgat   1260
ccttctaccg tgtttaagga tggcgatgag gccgaggatt ttgtggaggt gcacctgcct   1320
gatgtgcata gcagatctc tggcgtggat ctgggcctgc ctaactgggg aaagtaccat   1380
caccaccacc accactaa                                                 1398

SEQ ID NO: 3             moltype = AA   length = 465
FEATURE                  Location/Qualifiers
source                   1..465
                         mol_type = protein
                         organism = synthetic construct
SEQUENCE: 3
MIPQVLLFVP LLVFSSCFGK FPIYTIPDKL GPWSPIDIHH LSCPNNLVVE DEGCTNLSGF    60
SYMELKVGYI SAIKVNGFTC TGVVTEAETY TNFVGYVTTT FKRKHFRPMP DACRAAYNWK   120
MAGDPRYEES LHNPYPDYHW LRTVKTTKES LVIISPSVAD LDPYDKSLHS RVFPGGKCSG   180
ITVSSTCCST NHDYTIWMPE NPRLGTSCDI FTNSRGKRAS KGGKTCGFVD ERGLYKSLKG   240
ACKMKLCGVL GLRLMDGTWV AIQTSDEIKW CSPDQLVNLH DFHSDEIEHL VVEELVKKRE   300
ECLDALETIM TTKSVSFRRL SHLRKLVPGF GKAYTIFNKT LMEADAHYKS IRTWNEIIPS   360
KGCLRVGGRC HPHVNGVFFN GIILGPDGHV LIPEMQSSLL HQHMELLESS VIPLMHPLAD   420
PSTVFKDGDE AEDFVEVHLP DVHKQISGVD LGLPNWGKYH HHHHH                   465
```

What is claimed is:

1. A monoclonal antibody 2F2 that specifically binds rabies virus G proteins, comprising the amino acid sequence of SEQ ID No. 1.

2. A universal rabies virus antibody rapid detection test paper, comprising: a sample pad, a binding pad, a detection membrane and a water absorption pad sequentially overlapped on a support plate, wherein a test line and a quality control line are sprayed on the detection membrane; and the antibody of claim 1 is sprayed as an antibody solution on the quality control line.

3. The test paper of claim 2, wherein the antibody solution is sprayed at a concentration of 0.5 mg/mL.

4. The test paper of claim 3, wherein the antibody solution is sprayed at a concentration of 1 μL/cm.

5. The test paper of claim 2, wherein the binding pad is sprayed with colloidal gold-labeled rabies virus G proteins.

6. The test paper of claim 5, wherein the colloidal gold-labeled rabies virus G proteins are sprayed in a form of a rabies virus G protein solution at a concentration of 1 mg/ml; or 15 μL/cm.

7. The test paper of claim 2, wherein a distance between the quality control line and the test line is 0.5 cm.

8. The test paper of claim 2, wherein an overlapping distance of an overlap joint is 1-2 mm.

\* \* \* \* \*